US00PP26150P2

(12) United States Plant Patent
Laughner

(10) Patent No.: US PP26,150 P2
(45) Date of Patent: Nov. 24, 2015

(54) ***OSTEOSPERMUM* PLANT NAMED 'BALOSTLUEYE'**

(50) Latin Name: *Osteospermum ecklonis*
Varietal Denomination: Balostlueye

(71) Applicant: Ball Horticultural Company, West Chicago, IL (US)

(72) Inventor: Linda Laughner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 114 days.

(21) Appl. No.: 13/999,731

(22) Filed: Mar. 18, 2014

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Annette Para
(74) *Attorney, Agent, or Firm* — Audrey Charles

(57) ABSTRACT

A new and distinct cultivar of *Osteospermum* plant named 'Balostlueye', characterized by its medium yellow and dark purple colored inflorescences, medium green-colored foliage, and moderately vigorous, upright-mounded growth habit, is disclosed.

1 Drawing Sheet

Latin name of genus and species of plant claimed: *Osteospermum ecklonis*.
Variety denomination: 'Balostlueye'.

BACKGROUND OF THE INVENTION

The present invention relates to a new and distinct cultivar of *Osteospermum* plant botanically known as *Osteospermum ecklonis* and hereinafter referred to by the cultivar name 'Balostlueye'.

The new cultivar originated in a controlled breeding program in Santa Paula, Calif. during July 2011. The objective of the breeding program was the development of *Osteospermum* cultivars that are freely flowering with unique flower coloration and a freely branching, upright-mounded growth habit.

The new *Osteospermum* cultivar is the result of cross-pollination. The female (seed) parent of the new cultivar is the proprietary *Osteospermum ecklonis* breeding selection coded 49249-5, not patented, characterized by its dark yellow and lavender colored inflorescences, medium green-colored foliage, and moderately vigorous, compact-mounded growth habit. The male (pollen) parent of the new cultivar is the proprietary *Osteospermum ecklonis* breeding selection coded 49305-4, not patented, characterized by its light yellow-colored inflorescences that age to a frosted purple, medium green-colored foliage, and moderately vigorous, mounded growth habit. The new cultivar was discovered and selected as a single flowering plant within the progeny of the above stated cross-pollination during April 2012 in a controlled environment in Santa Paula, Calif.

Asexual reproduction of the new cultivar by terminal stem cuttings since April 2012 in Santa Paula, Calif., Arroyo Grande Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balostlueye' as a new and distinct cultivar of *Osteospermum* plant:

1. Medium yellow and dark purple colored inflorescences;
2. Medium green-colored foliage; and
3. Moderately vigorous, upright-mounded growth habit.

Plants of the new cultivar differ from plants of the female parent primarily in having larger inflorescences and wider ray florets and from plants of the male parent primarily in inflorescences color and in having longer peduncles.

Of the many commercially available *Osteospermum* cultivars, the most similar in comparison to the new cultivar is Side Show Golden Yellow 'Saksisgolye', U.S. Plant Pat. No. 19,602. However, in comparison, plants of the new cultivar differ from plants of 'Saksisgolye' in at least the following characteristics:

1. Plants of the new cultivar have a ray floret color different from plants of 'Saksisgolye';
2. Plants of the new cultivar have a disc floret color different from plants of 'Saksisgolye'; and
3. Plants of the new cultivar have larger diameter inflorescences than plants of 'Saksisgolye'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balostlueye'. The plants were grown in 4-inch pots for 11 weeks in a greenhouse in West Chicago, Ill. Plants were given one pinch at transplant.

DETAILED BOTANICAL DESCRIPTION

Figure 1:
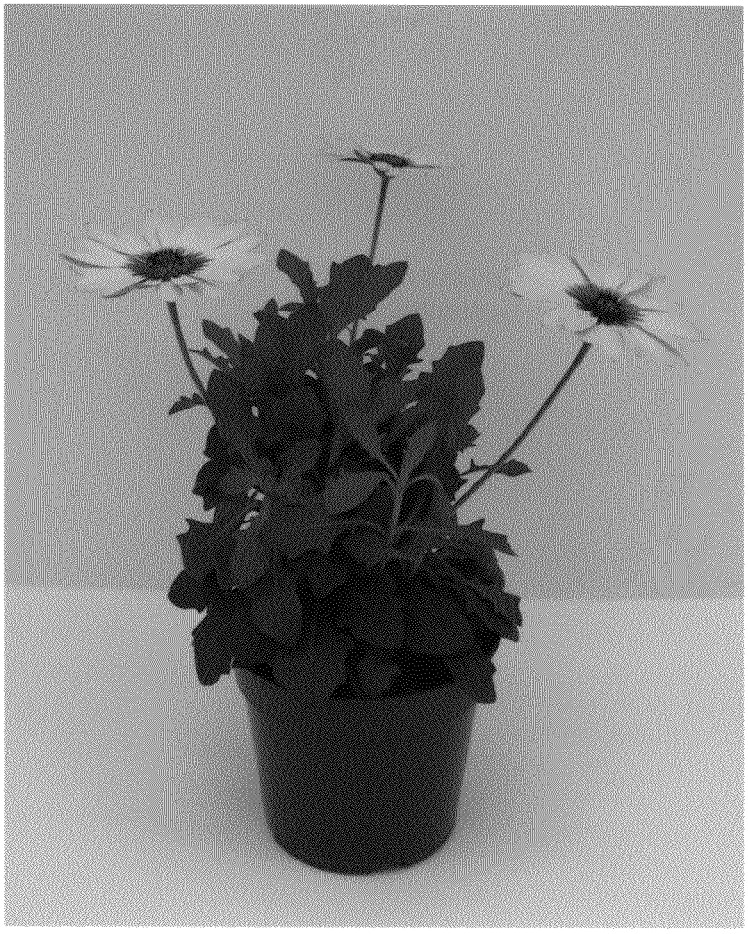
FIG. 1 illustrates a side view of the overall growth and flowering habit of 'Balostlueye'.
Figure 2:
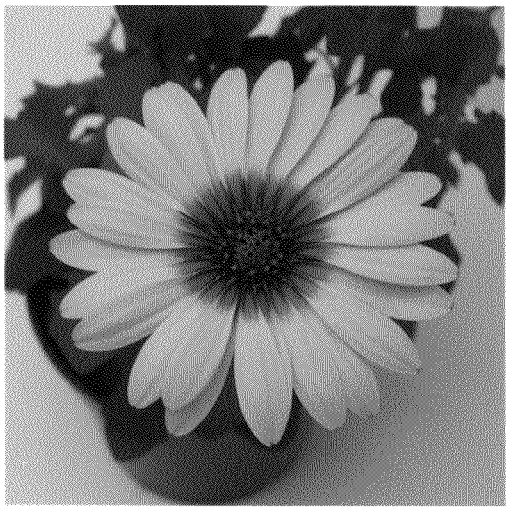
FIG. 2 illustrates a close-up view of an individual inflorescence of 'Balostlueye'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in January 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 11 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Osteospermum ecklonis* cultivar Balostlueye.

Parentage:

*Female parent*.—Proprietary *Osteospermum ecklonis* breeding selection coded 49249-5, not patented.

*Male parent*.—Proprietary *Osteospermum ecklonis* breeding selection coded 49305-4, not patented.

Propagation:

*Type cutting*.—Terminal stem.

*Time to initiate roots*.—Approximately 9 to 12 days.

*Time to produce a rooted cutting*.—Approximately 28 to 32 days.

*Root description*.—Fibrous.

*Rooting habit*.—Freely branching.

Plant description:

*Commercial crop time*.—Approximately 10 to 13 weeks from a rooted cutting to finish in a 10 cm pot.

*Growth habit and general appearance*.—Moderately vigorous, upright-mounded.

*Size*.—Height from soil level to top of plant plane: Approximately 16.5 cm. Width: Approximately 19.5 cm.

*Branching habit*.—Freely branching, pinching enhances basal branching. Quantity of main branches per plant: Approximately 3.

*Branch*.—Strength: Strong. Length to base of peduncle: Approximately 7.5 cm. Diameter: Approximately 3.0 mm. Length of central internode: Approximately 3.0 mm. Texture: Glabrous. Color of young and mature stems: 144B.

Foliage description:

*General description*.—Quantity of leaves per main branch: Approximately 7. Fragrance: Pungent. Form: Simple. Arrangement: Alternate.

*Leaves*.—Aspect: Acute angle to stem becoming an obtuse angle with age. Shape: Spatulate. Margin: Widely dentate. Apex: Acute. Base: Attenuate. Venation pattern: Pinnate. Length of mature leaf: Approximately 5.0 cm. Width of mature leaf: Approximately 3.0 cm. Texture of upper and lower surfaces: Sparsely pubescent. Color of upper surface of young and mature foliage: 137A with venation of 145B or indistinguishable. Color of lower surface of young and mature foliage: 138A with venation of 145A or indistinguishable.

*Petiole*.—Length: Approximately 1.5 cm. Diameter: Approximately 4.0 mm. Texture: Mixture of glandular and non-glandular pubescence. Gland color: Colorless. Color: 145A.

Flowering description:

*Flowering habit*.—'Balostlueye' is freely flowering under outdoor growing conditions with substantially continuous blooming from spring through autumn and year-round in greenhouse environment.

*Lastingness of individual inflorescence on the plant*.—Approximately 8 to 10 days.

Inflorescence description:

*General description*.—Type: Solitary, composite. Persistent. Shape: Round. Aspect: Facing upward. Arrangement: Terminal, held above the foliage, arising from leaf axils. Disc and ray florets develop acropetally on a capitulum. Fragrance: Faint. Quantity per plant: Approximately 3. Diameter: Approximately 6.8 cm. Depth: Approximately 1.6 cm.

*Peduncle*.—Strength: Strong. Aspect: Erect. Length: Approximately 10.5 cm. Diameter: Approximately 2.0 mm. Texture: Glandular pubescent. Gland color: Colorless. Color: 144A.

*Bud*.—Rate of opening: Generally takes 4 to 6 days for bud to progress from first color to fully open flower. Quantity per plant: Approximately 1.

*Bud just before opening*.—Shape: Ovoid. Length: Approximately 1.3 cm. Diameter: Approximately 1.1 cm. Color: 154B.

*Ray florets*.—Quantity per inflorescence: Approximately 26. Arrangement: Imbricate in a single whorl. Aspect: Initially at acute angle to disc, becoming perpendicular at maturity and downward turning as senesce. Shape: Oblanceolate. Margin: Entire. Apex: Emarginate with three tips. Base: Attenuate. Length: Approximately 3.3 cm. Width: Approximately 8.0 mm. Texture of upper surface: Glabrous. Texture of lower surface: Glabrous with a densely pubescent base. Color of upper surface when first open: 4B with base of N79B. Color of lower surface when first and fully open: 4D with overlay of 177B and base of N79C. Color of upper surface when fully open: 4B with base of N79C.

*Disc florets*.—Quantity per inflorescence: Approximately 90. Arrangement: Massed in center of inflorescence. Shape: Tubular. Margin: Entire. Apex: Five acute tips. Base: Attenuate, fused. Length: Approximately 9.0 mm. Diameter at apex: Approximately 2.0 mm. Diameter at base: Approximately 1.0 mm. Texture: Glabrous with a sparsely pubescent outer surface. Color when fully open: NN155A with tips of N92A and base of 145D.

*Disc*.—Diameter: Approximately 1.4 cm. Depth: Approximately 6.0 mm.

*Receptacle*.—Shape: Conical. Height: Approximately 2.0 mm. Diameter: Approximately 4.0 mm. Color: 145D.

*Phyllaries*.—Quantity per inflorescence Approximately 20. Arrangement: In a single whorl. Shape: Linear to lanceolate. Margin: Entire. Apex: Acute. Base: Truncate. Length: Approximately 9.0 mm. Width: Approximately 1.0 mm. Texture of upper or inner surface: Glabrous. Texture of lower or outer surface: Mixture of glandular and non-glandular pubescence. Gland color: Colorless. Color of upper or inner surface: 138B. Color of lower or outer surface: 138A.

*Reproductive organs*.—Androecium: Present on disc florets only. Stamen quantity: 5 per floret, fused around the style. Stamen length: Approximately 4.0 mm. Anther shape: Linear. Anther length: Approximately 2.0 mm. Anther color: N186A. Pollen amount: Abundant. Pollen color: 21A. Gynoecium: Present on ray and disc florets. Pistil quantity: 1 per floret. Pistil length: Approximately 9.0 mm. Stigma shape: Rounded. Stigma length: Less than 1 mm. Stigma color: N92A. Style length: Approximately 6.0 mm. Style color: NN155D. Ovary length: Approximately 3.0 mm. Ovary color: 145D.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Balostlueye', substantially as herein shown and described.

* * * * *